(12) United States Patent
Risch

(10) Patent No.: US 11,890,214 B2
(45) Date of Patent: Feb. 6, 2024

(54) PROCESS FOR MACHINE REPOSITIONING OF A PRE-CRIMPED DRUG-COATED STENT

(71) Applicant: BIOTRONIK AG, Bülach (CH)

(72) Inventor: Fabian Risch, Doerflingen (CH)

(73) Assignee: BIOTRONIK AG, Buelach (CH)

( * ) Notice: Subject to any disclaimer, the term of this patent is extended or adjusted under 35 U.S.C. 154(b) by 296 days.

(21) Appl. No.: 17/294,632

(22) PCT Filed: Nov. 19, 2019

(86) PCT No.: PCT/EP2019/081796
§ 371 (c)(1),
(2) Date: May 17, 2021

(87) PCT Pub. No.: WO2020/109081
PCT Pub. Date: Jun. 4, 2020

(65) Prior Publication Data
US 2022/0008236 A1     Jan. 13, 2022

(30) Foreign Application Priority Data

Nov. 27, 2018   (DE) .......................... 102018129919.2

(51) Int. Cl.
*B23P 19/10*     (2006.01)
*A61F 2/95*     (2013.01)

(52) U.S. Cl.
CPC .................................. *A61F 2/9524* (2020.05)

(58) Field of Classification Search
CPC .............. A61F 2/9524; A61F 2/9522; A61F 2250/0008; A61F 2250/0098; A61F 2/958; A61F 2002/9534; A61M 25/10; A61M 25/104; Y10T 29/4994; Y10T 29/49929; Y10T 29/53987; Y10T 29/53996

See application file for complete search history.

(56) References Cited

U.S. PATENT DOCUMENTS

| 2006/0183383 A1 | 8/2006 | Asmus et al. |
| 2010/0143526 A1* | 6/2010 | Stenzel ................. A61F 2/9524 425/363 |
| 2012/0010693 A1* | 1/2012 | Van Sciver ............. A61F 2/958 623/1.11 |
| 2015/0292872 A1* | 10/2015 | Tripp ..................... G01B 11/14 356/601 |

OTHER PUBLICATIONS

International Search Report and Written Opinion from the corresponding International Patent Application No. PCT/EP2019/081796, dated Jan. 24, 2020.

* cited by examiner

*Primary Examiner* — Jun S Yoo
(74) *Attorney, Agent, or Firm* — Greer, Burns & Crain, Ltd.; Steven P. Fallon

(57) ABSTRACT

A process for repositioning a drug-coated stent that is pre-crimped on a balloon of a balloon catheter extending in an axial direction so that an inner surface of the stent lies against an outer surface of the balloon. The stent is gripped with at least one contact element and a protection device between the stent and the at least one contact element to prevent contact between the stent and the at least one contact element. The stent is moved with the at least one contact element in the axial direction with respect to the balloon of the balloon catheter to reposition the stent with respect to the balloon.

19 Claims, 9 Drawing Sheets

US 11,890,214 B2

PROCESS FOR MACHINE REPOSITIONING OF A PRE-CRIMPED DRUG-COATED STENT

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/081796, which was filed Nov. 19, 2019, which application claimed priority from German Application Serial Number 10 2018 129 919, which was filed Nov. 27, 2018.

FIELD OF THE INVENTION

This invention relates to a process for repositioning a stent that is pre-crimped on a balloon of a balloon catheter.

BACKGROUND

As a rule, such repositioning of a stent is done so that the stent sits in an exactly defined position with respect to the balloon of the balloon catheter, so that during implantation its position can be identified, e.g., using X-ray markers arranged on the balloon catheter, and a defined expansion of the stent by the balloon is possible.

In the prior art, such repositioning of stents by manual means is known, the stent in question being manually moved or repositioned, e.g., by gloves. Furthermore, machine repositioning of non-drug-coated stents is known, which involves making contact with and moving the stent by a mechanical gripping mechanism.

Furthermore, EP 1807021 describes a process wherein the stent is arranged between two films as it is crimped on a catheter, these two films essentially surrounding the stent.

Furthermore, EP 2590601 discloses a process for arranging a stent on a balloon using a fork to project into the proximal end of the stent and push the stent forward over the balloon.

During automated processing of drug-coated stents, it is necessary to prevent cross contamination. To accomplish this, the components of a device used for repositioning that come in contact with the stent must be either cleaned or replaced after every product run. This makes machine repositioning of the stent very laborious, and thus cost-intensive.

During an angioplasty procedure, such a stent is used, e.g., to keep open a vessel of a patient, the stent being transported to the implantation site by the balloon catheter and anchored in the vessel by expanding the balloon. Furthermore, drug-coated indicates that the stent is coated with at least one drug that is delivered to the patient's body, e.g., after implantation of the stent.

SUMMARY OF THE INVENTION

A process for repositioning a drug-coated stent that is pre-crimped on a balloon of a balloon catheter extending in an axial direction so that an inner surface of the stent lies against an outer surface of the balloon. The stent is gripped with at least one contact element and a protection device between the stent and the at least one contact element to prevent contact between the stent and the at least one contact element. The stent is moved with the at least one contact element in the axial direction with respect to the balloon of the balloon catheter to reposition the stent with respect to the balloon.

BRIEF DESCRIPTION OF THE DRAWINGS

Sample embodiments of the invention and features and advantages of this invention are explained below using the figures. The figures are as follows.

DETAILED DESCRIPTION OF THE PREFERRED EMBODIMENTS

Figure 1:
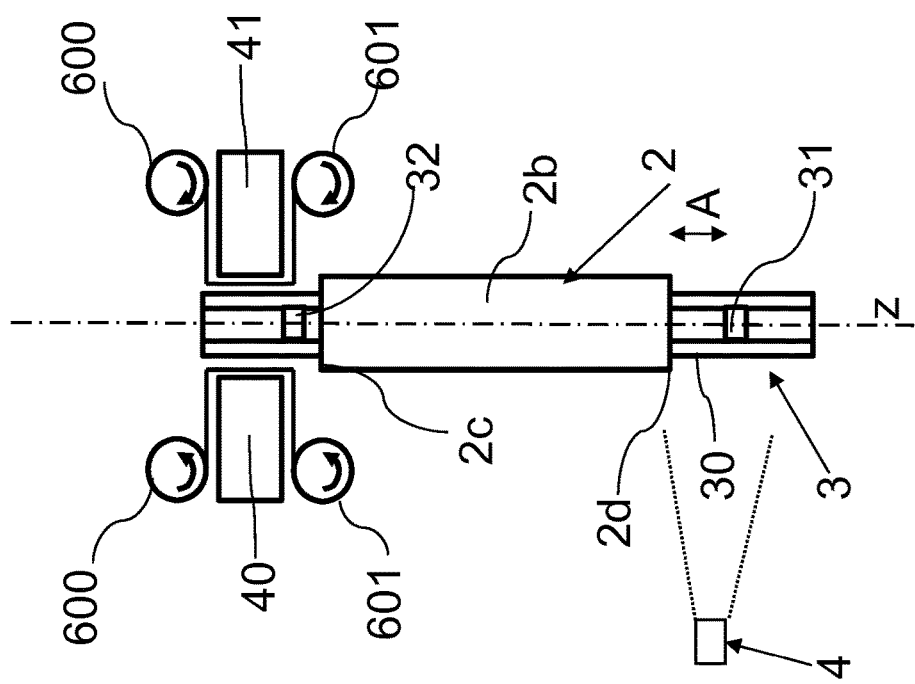
FIG. 1 an embodiment of the inventive process or an inventive device for repositioning a drug-coated stent with respect to a balloon of a balloon catheter, direct contact between contact elements and the stent being prevented by films.

One embodiment of the process provides that the at least one contact element be moved out of a first position toward the balloon catheter into a second position, so that at least one contact element reaches behind a face of the stent with the protection device between them or that, to grip the stent, this contact element presses against the stent with the protection device between them.

One embodiment of the process further provides that, to reposition the stent, the at least one contact element located in the second position be moved in the axial direction along the balloon catheter, carrying the stent along, the balloon catheter being fixed in the axial direction. Another embodiment of the process provides that to reposition the stent in the axial direction along the balloon catheter, the balloon catheter is pulled in the proximal direction by the at least one contact element, which holds the stent in position, preferably at the distal section of the stent, in the axial direction, thereby fixing it.

One embodiment of the process further provides that to reposition the stent it is moved in the axial direction until the distance in the axial direction from one end of the stent to an X-ray marker arranged on the balloon catheter corresponds to a predefined distance. Preferably, this end of the stent is the distal end of the stent. Furthermore, the X-ray marker is preferably a distal X-ray marker. Here distal means that the component referred to as distal is arranged remote from a person handling the balloon catheter during the implantation, this person operating the balloon catheter from a proximal end of the balloon catheter. Therefore, a proximal end of the stent is arranged closer, along the balloon catheter, to the aforementioned person than the distal end is. This also applies for the position of a proximal X-ray marker that might be present with respect to the distal X-ray marker.

One embodiment of the process further provides that the protection device have at least one flexible film, the at least one contact element gripping the stent with the at least one film between them, to prevent contact between the stent and the at least one contact element. The film can have, e.g., PTFE or can consist of PTFE.

One embodiment of the process further provides that after the at least one film makes contact with the stent, it is moved so that a stent that is subsequently to be repositioned by the at least one contact element makes contact with a section of the at least one film, this section not yet previously having been in contact with the stent.

One embodiment of the process further provides that the at least one film be moved in the axial direction of the balloon catheter, or that the film be moved in a direction orthogonal to the axial direction.

One embodiment of the process further provides that the at least one film be moved by unwinding the film from a feed roller and winding it up onto a take-up roller.

One embodiment of the process further provides that, to reposition the stent with respect to the balloon, the stent be moved, by multiple contact elements, in the axial direction with respect to the balloon of the balloon catheter, and that, to reposition the stent, each of the contact elements grip it with an associated film (e.g., made of PTFE) between the contact element and the stent, to prevent contact between the stent and the respective contact element, in particular the respective contact element being moved out of a first position toward the balloon catheter into a second position, so that the respective contact element reaches behind a face of the stent with the associated film between them, or that, to grip the stent, this contact element presses against the stent with the associated film between them (in order to grip the stent, e.g., at a middle or distal section of the stent), in particular, to reposition the stent the respective contact element located in the second position being moved along the balloon catheter, carrying along the stent with it.

It is advantageous to grip the stent, by the at least one contact element, at a middle, preferably at a distal section of the stent for repositioning. The repositioning can be done either by pulling the stent in distal direction or by holding the stent and pulling the balloon catheter in proximal direction repositioning the stent in distal direction on the catheter. Such way of repositioning results in rather a stretching of the stent when being repositioned in contrast to a compression which would occur when the stent is held by a contact element at the proximal section or front side of the stent. Compressing the stent could lead to an irreversible staggering of stent struts which could damage the balloon during the following crimping process. Hence, performing the repositioning a way which leads to stretching of the stent is favorable as catheter rejections due to defects can be reduced which further is cost efficient.

Here it is also possible for the respective film to be moved after contact with the stent, so that a stent that is subsequently to be repositioned makes contact with a section of the respective film, this section not yet previously having been in contact with the stent.

The respective film can be moved in the axial direction of the balloon catheter, or in a direction orthogonal to the axial direction. Furthermore, the respective film can once again be moved by unwinding the respective film from a feed roller and winding it up onto a take-up roller.

One embodiment of the process further provides that the distance be monitored with a camera. Alternatively, it is possible to use a capacitive sensor or an inductive sensor.

An output signal of the camera or of the sensor can be used to control, by open-loop control or closed-loop control, the movement of the stent or of the at least one or of the multiple contact elements in the axial direction. Here it is advantageous if the at least one or the multiple contact elements are moved and the balloon catheter is held stationary, i.e., if it is at rest. If a camera is used, the distance between stent and X-ray marker can be calculated, for example, from the number of pixels between the features stent and X-ray marker, which are recognized by the camera, by multiplying this number by the "mm/pixel" value that is known from the camera calibration. A distance between marker and stent defined in this way as the actual distance is compared with a desired distance. The difference determines the advancement of the contact elements, and thereby that of the stent.

A priority method of calculating the desired distance is by having the camera measure the distance between the X-ray markers to one another and the length of the stent.

Furthermore, before the stent is repositioned it is preferably pre-crimped so that it has an offset in a defined direction, so that when the stent is repositioned it only has to be moved in the opposite direction, which corresponds to the direction of motion of the at least one contact element or of the multiple contact elements.

After the stent is repositioned, it can be fixed in final position by crimping it again on the balloon of the balloon catheter.

One embodiment of the process further provides that the protection device be formed by a protective sheath arranged on the stent and surrounding the stent, the at least one contact element gripping the stent with the protective sheath between them, to prevent contact between the stent and the at least one contact element. The protective sheath preferably covers the outer surface of the stent, and especially the ends or faces of the stent.

One embodiment of the process further provides that, to reposition the stent with respect to the balloon, the stent be moved, by multiple contact elements, in the axial direction with respect to the balloon of the balloon catheter, and that, to reposition the stent, the contact elements grip it with the protective sheath between them and the stent, to prevent contact between the stent and the contact elements, in particular the respective contact element being moved out of a first position toward the balloon catheter into a second position, so that the respective contact element reaches behind a face of the stent with the protective sheath between them, or that, to grip the stent, this contact element presses against the stent with the protective sheath between them (in order to grip the stent, e.g., at a middle section of the stent), in particular, to reposition the stent the respective contact element located in the second position being moved along the balloon catheter, carrying the protective sheath and the stent along with it.

One embodiment of the process further provides that the position of the stent be determined by a capacitive or an inductive sensor.

A capacitive or an inductive sensor is particularly preferred when protective sheath is used as protection device. Given that the stent inside the protective sheath cannot be visually detected a capacitive or an inductive sensor provides for identifying the position of the stent inside the protective sheath. A camera could not be used in such case. Therefore, for the process as suggested herein it is preferred to provide a capacitive or an inductive sensor when a protective sheath is used.

One embodiment of the process further provides that before the stent is moved in the axial direction, the balloon catheter is moved in the axial direction until the sensor detects the aforementioned X-ray marker and the aforementioned end of the stent. Alternatively, it is also possible for the sensor to be moved until it detects the aforementioned X-ray marker and the aforementioned end of the stent. That is, it is only after this detection that, to reposition the stent, the stent is moved in the axial direction until the distance in the axial direction from the end of the stent to the X-ray marker corresponds to the predefined distance.

Here again, before the stent is repositioned it is preferably pre-crimped so that it has an offset in a defined direction, so that when the stent is repositioned it only has to be moved in the opposite direction, which corresponds to the direction of motion of the at least one contact element or of the multiple contact elements.

After the stent is repositioned, it can once again be fixed in final position by crimping it again on the balloon of the balloon catheter.

Another aspect of this invention relates to a device for repositioning a drug-coated stent that is pre-crimped on a balloon of a balloon catheter extending in an axial direction, so that an inner surface of the stent lies against an outer surface of the balloon, the device having at least one contact element that is configured to move the stent in the axial direction with respect to the balloon of the balloon catheter in order to reposition the stent with respect to the balloon, and, to reposition the stent, the at least one contact element being configured to grip the stent with the protection device of the device between them, to prevent contact between the stent and the at least one contact element.

One embodiment of the device provides that the at least one contact element be configured to be moved out of a first position toward the balloon catheter into a second position, if balloon catheter is arranged with respect to the at least one contact element in the way it is supposed to be, so that the at least one contact element reaches behind a face of the stent with the protection device between them, or that, to grip the stent, this contact element presses against the stent with the protection device between them.

One embodiment of the device further provides that the at least one contact element has, to reach behind the stent, a tapering end section.

Furthermore, the at least one contact element is preferably designed so that if it is located in the second position, in order to reposition the stent, it is moved in the axial direction along the balloon catheter, in order to carry along the stent (if the balloon catheter is fixed with respect to the axial direction).

One embodiment of the device further provides that the device be configured, in order to reposition the stent, to move the stent in the axial direction until the distance in the axial direction from one end of the stent to an X-ray marker arranged on the balloon catheter corresponds to a predefined distance.

Another embodiment of the device provides that the protection device have at least one film, the at least one contact element being designed to grip the stent with the at least one film between them, to prevent contact between the stent and the at least one contact element.

One embodiment of the device further provides that the at least one film be designed to be moved after contact with the stent, so that a stent that is subsequently to be repositioned makes contact with one section of the at least one film, this section not previously having been in contact with the stent.

One embodiment of the device provides that the at least one film be configured to be moved in the axial direction of the balloon catheter or in a direction orthogonal to the axial direction.

One embodiment of the device further provides that the device for moving the at least one film have a feed roller, from which the at least one film can be unwound, and a take-up roller, onto which the at least one film can be wound up. This can also be accomplished by moving the contact elements.

Another embodiment of the inventive device provides that the device be configured to move the stent, by multiple contact elements, in the axial direction with respect to the balloon of the balloon catheter, in order to reposition the stent with respect to the balloon, each of the contact elements for repositioning the stent being configured to grip the stent with each of the contact elements having, between it and the stent, a film of the device, to prevent contact between the stent and the contact elements, in particular the respective contact element being designed to be moved out of a first position toward the balloon catheter into a second position, when the balloon catheter is arranged with respect to the contact elements in the way it is supposed to be, so that the respective contact element reaches behind a face of the stent with a film of the device between them, or that, to grip the stent, this contact element presses against the stent with the protection device between them, in particular to reposition the stent the respective contact element located in the second position being designed to be moved in order to carry along the stent (if the balloon catheter is fixed with respect to the axial direction).

One embodiment of the device further provides that the device have a camera to monitor the aforementioned distance between the end of the stent and the X-ray marker. Instead of a camera, it is possible to use an inductive or a capacitive sensor, especially when the position of the stent cannot be visually determined, for example if the view of the stent is blocked.

One alternative embodiment of the device further provides that the protection device be formed by a protective sheath to be arranged on the stent and surround the stent, the at least one contact element being configured to grip the stent with the protective sheath between them, when the protective sheath is arranged with respect to the stent in the way it is supposed to be, to prevent contact between the stent and the at least one contact element.

One embodiment of the device further provides that, to reposition the stent, the contact elements be configured to grip it with the protective sheath between the contact elements and the stent, when the protective sheath is arranged on the stent in the way it is supposed to be, to prevent contact between the stent and the contact elements, in particular the respective contact element being designed to be moved out of a first position toward the balloon catheter into a second position, when the balloon catheter is arranged with respect to the contact element in the way it is supposed to be, so that the respective contact element reaches behind a face of the stent with the protective sheath between them, or that, to grip the stent, this contact element presses against the stent with the protection device between them, in particular to reposition the stent the respective contact element located in the second position being designed to be moved in order to carry along the stent (if the balloon catheter is fixed with respect to the axial direction).

One embodiment of the device further provides that the device for determining the distance between the end of the stent and the X-ray marker have a capacitive or an inductive sensor (especially if the protective sheath is used).

A capacitive or an inductive sensor is particularly preferred when protective sheath is used as protection device. Given that the stent inside the protective sheath cannot be visually detected a capacitive or an inductive sensor provides for identifying the position of the stent inside the protective sheath. A camera could not be used in such case. Therefore, for the device as suggested herein it is preferred to include a capacitive or an inductive sensor when a protective sheath is used.

One embodiment further provides that the device be designed to move the balloon catheter in the axial direction with respect to the sensor until the sensor detects the aforementioned X-ray marker and the aforementioned end of the stent, and to do this before the stent is moved in the axial direction.

FIGS. 1 through 7 show different embodiments of a process or of a device for repositioning a drug-coated stent 2, which is pre-crimped on a balloon 30 of a balloon catheter 3. Stent 2 can have a circumferential wall structure (not shown in detail here), which is formed, e.g., from multiple struts that are connected with one another, so that the wall structure has multiple cells bordered by struts. The balloon catheter 3 preferably has X-ray markers 31, 32, so that a position of the balloon catheter 3 can be determined during the implantation.

Before such a repositioning process, the stent 2 is guided, e.g., through a transport system, to a pre-crimping head or tool. The position of the stent 2 in the head is defined, e.g., by a mechanical stop. Then, the balloon catheter 3 moves into the head and through the stent 2. The position of the stent 2 relative to the X-ray markers 31, 32 is now roughly defined by the travel path of the catheter 3. The stent 2 is preferably positioned with an offset to the proximal side. Then, the stent 2 is pre-crimped on the balloon 30, so that an inner surface 2a of the stent 2 lies tightly against an outer surface 30b of the balloon 30, however so that the stent 2 can still be moved with respect to the balloon 30. Furthermore, the stent 2 has, facing away from the inner surface 2a, an outer surface 2b whose drug coating must be protected from cross contamination.

As can be seen, e.g., from FIG. 1, one embodiment of the inventive process provides that at least one contact element, in this case, e.g., two contact elements 40, 41, move the stent 2 with respect to the balloon 30 in the axial direction z of the balloon catheter 3, in order to reposition stent 2 in a defined manner. Here it is provided that, to reposition the stent 2, the contact elements 40, 41 grip the stent 2 with at least one flexible film, which can consist, e.g., of PTFE, between each contact element 40, 41 and the stent, to prevent direct contact between the stent 2 and the respective contact element 40, 41.

To move or reposition the stent 2, the contact elements 40, 41 (see FIG. 1) are first moved toward one another until they reach behind a face 2c of the stent 2. Then, the contact elements 40, 41 are moved downward in the axial direction z, bumping against the face 2c of the stent 2, with the films 60, 61 between them, and carry stent 2 along, so that the stent is moved into a defined final position with respect to the balloon 30. A corresponding distance A between a stent end 2d and the distal X-ray marker 31 can be monitored by a camera 4 (or by an inductive or capacitive sensor).

Figure 2:
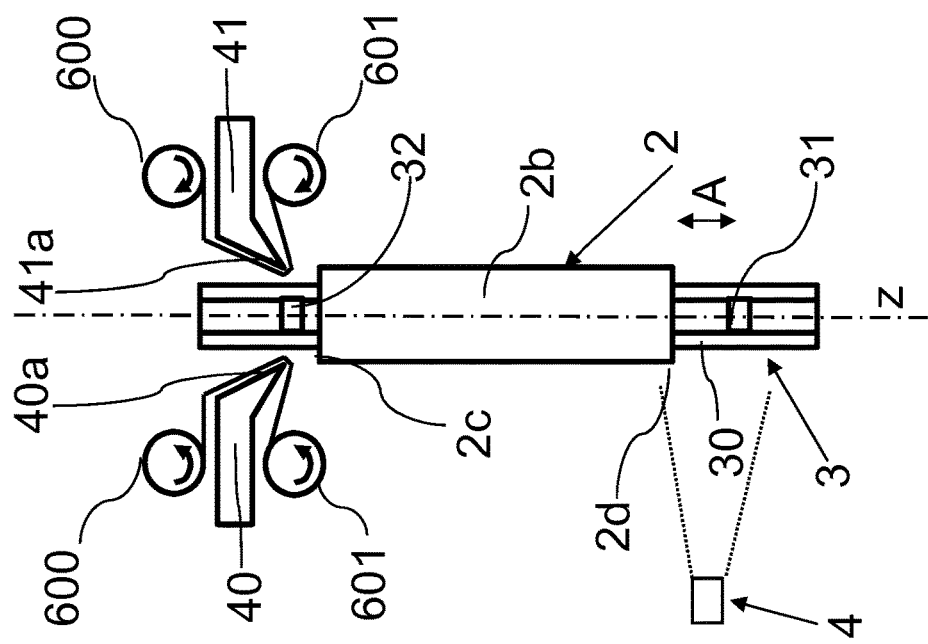
FIG. 2 a variation of the embodiment of the process or of the device for repositioning a drug-coated stent shown in FIG. 1.

FIG. 2 shows a variation of the device shown in FIG. 1, wherein the contact elements 40, 41 have, in contrast to [those in] FIG. 1, a tapering end section 40a, 41a to reach behind the stent 2.

As can also be seen in FIGS. 1 through 7, it is preferably provided that after the respective film 60, 61, 62 makes contact with the stent 2, this film 60, 61, 62 is moved, so that a stent that is subsequently to be repositioned makes contact with a section of the respective film 60 that had not previously been in contact with the stent 2, so that cross contamination of the stent 2 is prevented in a simple way.

Figure 3:
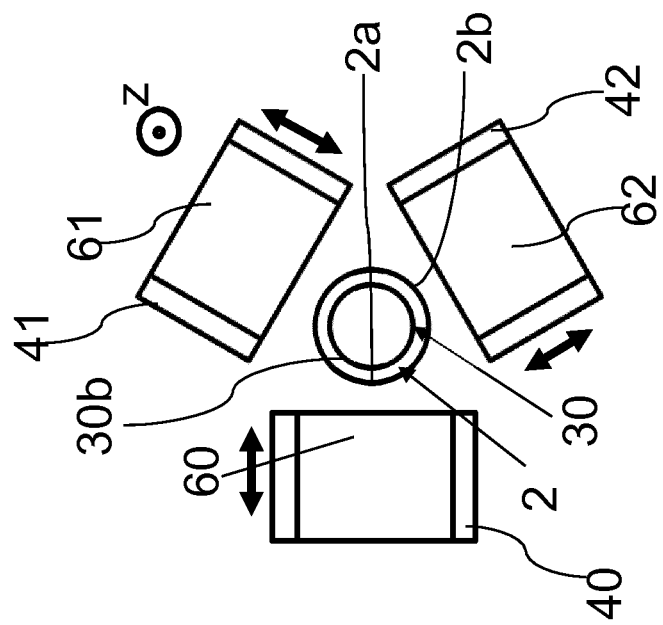
FIG. 3 a schematic representation of an arrangement of contact elements and films relative to one another or relative to the stent to be repositioned.
Figure 4:
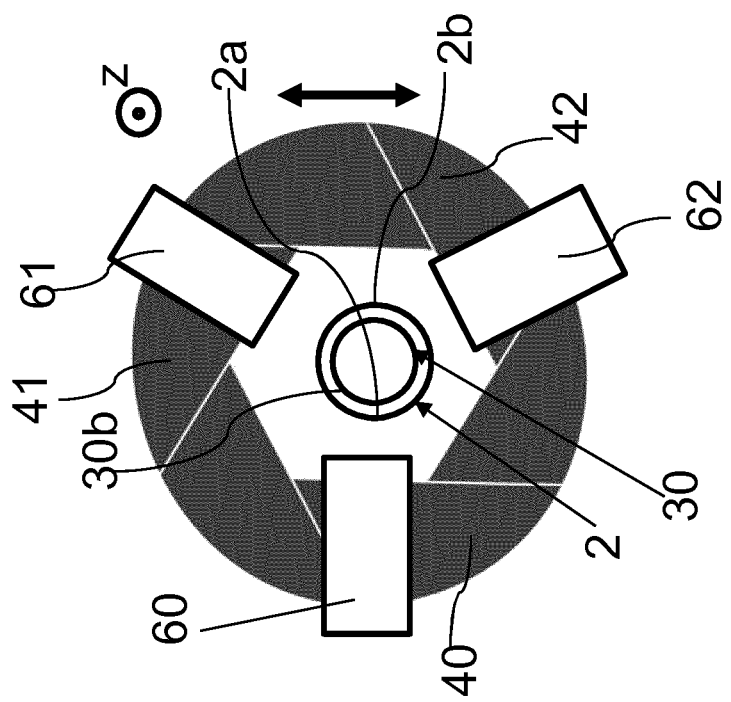
FIG. 4 a variation of the arrangement shown in FIG. 3.

The embodiments shown in FIGS. 3 and 4 provide that the respective film 60, 61, 62 is moved in the axial direction z of the balloon catheter 3. FIG. 3 shows an embodiment with three contact elements 40, 41, 42, which can be moved in the direction toward the catheter 3 to reach behind the face 2c of the stent 2, with the respective film 60, 61, 62 between them.

FIG. 4 shows multiple contact elements which lie against one another in the peripheral direction of the stent 2, forming a structure that encircles the stent 2 in the peripheral direction or surrounds the stent 2 in cross section. Each of three of the contact elements 40, 41, 42 is covered with a film 60, 61, 62, these films approaching one another when the contact elements are moved toward one another, with the final result that none of the contact elements can make direct contact with the stent 2, but rather can only reach behind or grip the stent 2 with the films 60, 61, 62 between them (see FIG. 7).

Figure 5:
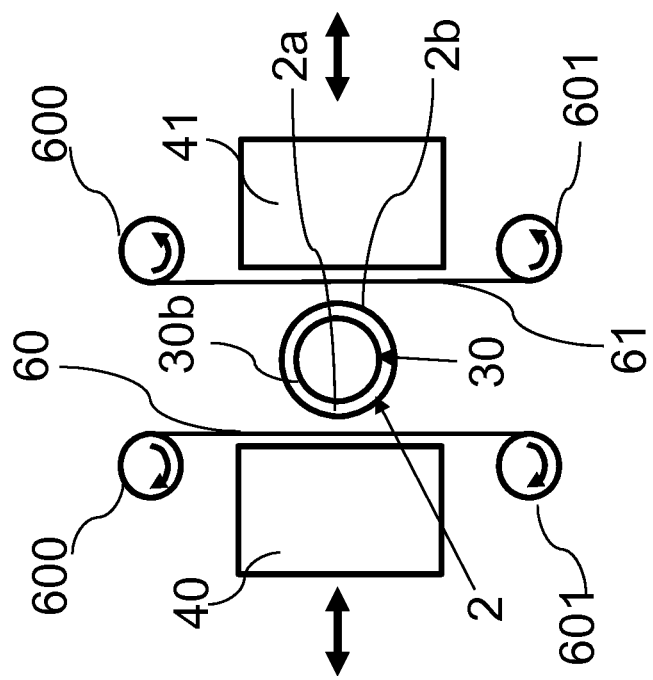
FIG. 5 a schematic sectional view of two contact elements that are opposite one another in a plane perpendicular to the axial direction of the balloon catheter.
Figure 6:
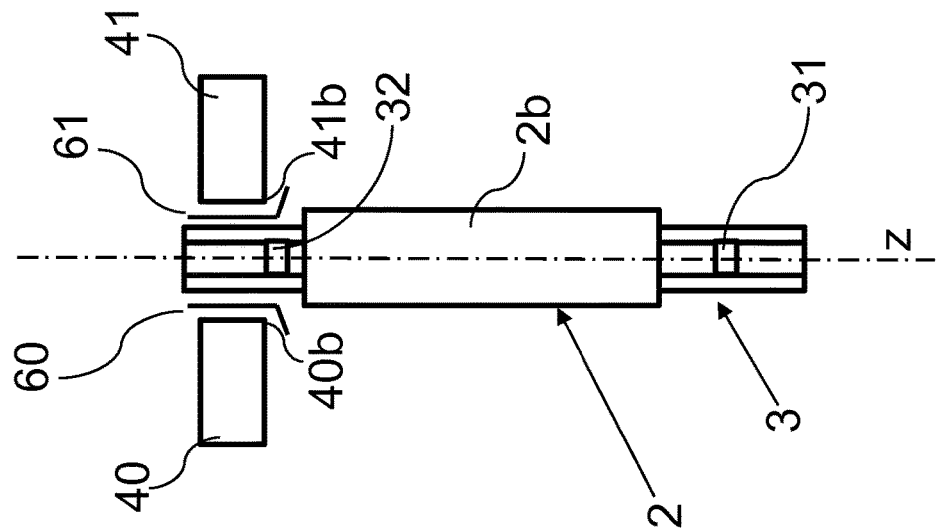
FIG. 6 another schematic sectional view of the contact elements according to FIG. 5.

Furthermore, FIGS. 5 and 6 show an embodiment in which the respective film 60, 61 is moved in a direction orthogonal to the axial direction z. Here it is possible, e.g., for the respective film 60, 61 to be turned around an edge 40b, 41b of the contact element 40, 41 in question, so that this edge 40b, 41b can be used to reach behind the stent 2 (see FIG. 6).

To move the respective film 60, 61, 62, it can be provided that the respective film 60, 61, 62 be unwound from a feed roller 600 and wound up onto a take-up roller 601. This can involve the respective take-up roller 601 being rotated or driven by a drive. Furthermore, it is also possible for the film to be unwound by moving the contact elements. Such a sequence of events could be supported, for example, by a spring ratchet system.

Figure 7:
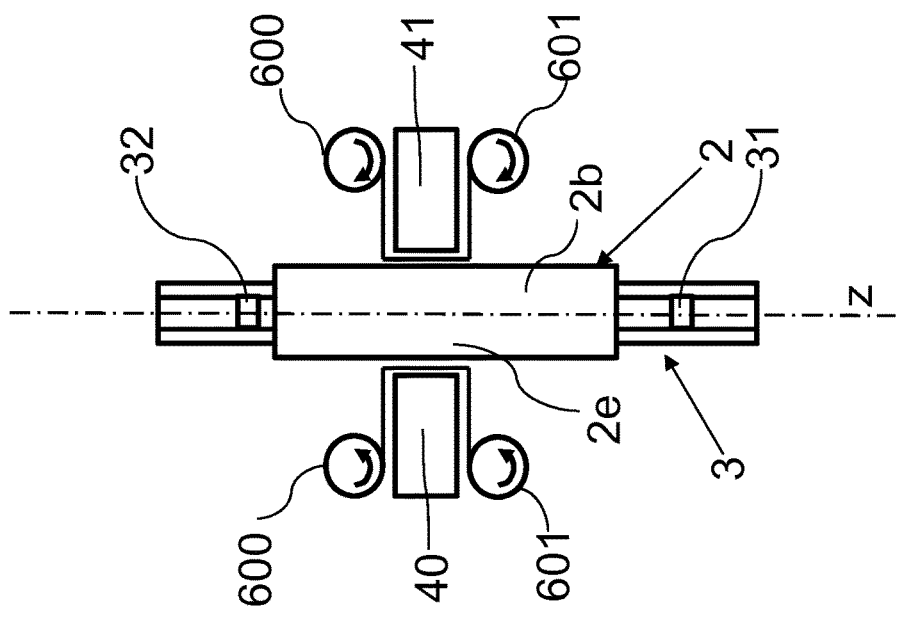
FIG. 7 a schematic representation of an embodiment of the process or of the device, wherein the stent is gripped or held in the middle by contact elements.

Instead of the contact elements 40, 41, and 42 reaching behind the stent 2, these contact elements 40, 41, and 42 can also be designed to grip, e.g., a middle section 2e of the stent 2 (with the respective film 60, 61, 62 between them), as is shown in FIG. 7.

After the stent 2 has been repositioned, it can be fixed in final position by crimping it again on the balloon 30 of the balloon catheter 3.

Furthermore, FIG. 8 shows an alternative embodiment of the inventive process or of the inventive device, wherein here the stent 2 is protected from making direct contact with the contact elements 40, 41 by encapsulating the stent 2 in a protective sheath 70, making cross contamination of the drug-coated stent 2 avoidable.

The aforementioned encapsulation should preferably remain over the entire process chain (in particular, transporting the stent, mounting the stent on the balloon, pre-crimping the stent, repositioning the stent, crimping the stent, embedding the stent), in order to avoid additional process steps for removing the encapsulation or the protective sheath 70.

Figure 8A:
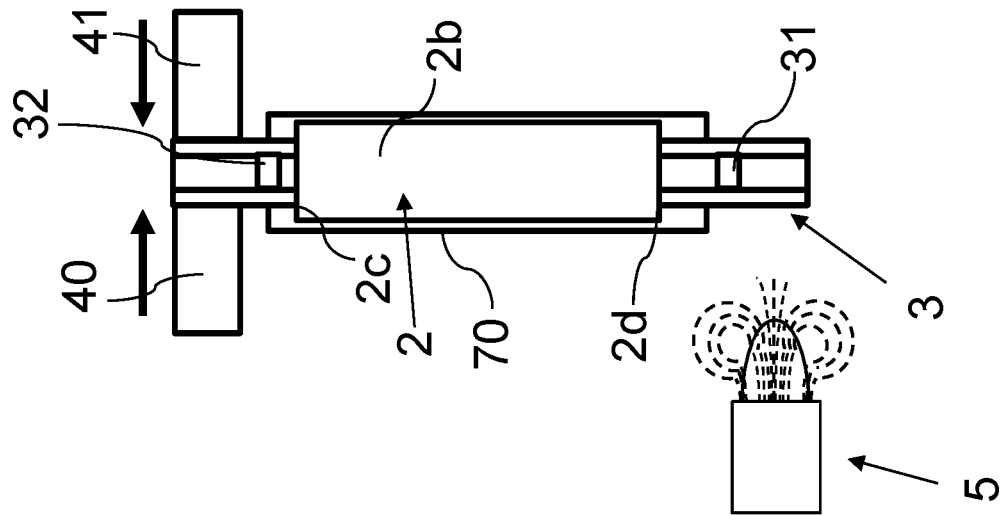
FIG. 8 a schematic representation of an alternative embodiment of an inventive process or of an inventive device, wherein here the drug-coated stent is protected from direct contact with the contact elements by a protective sheath.
Figure 8B:
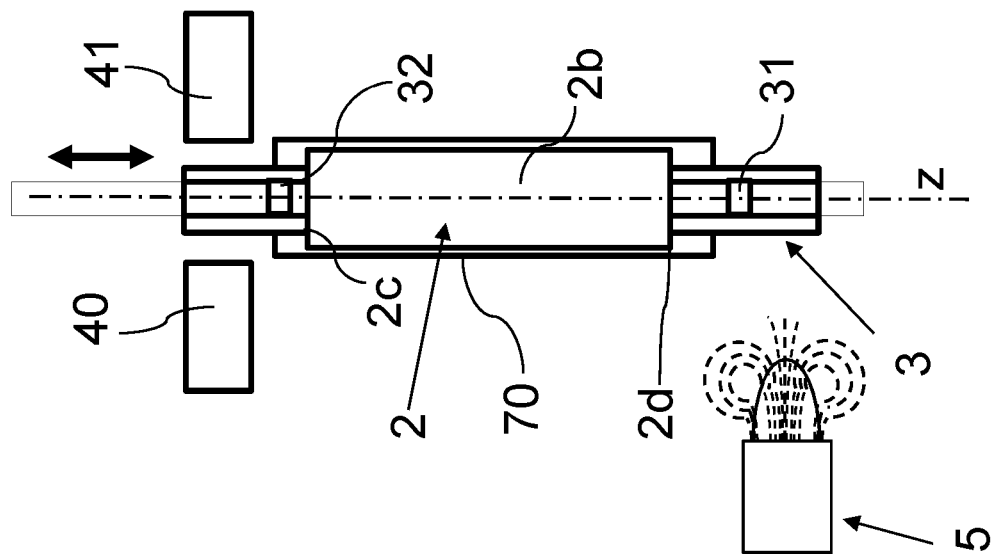
Figure 8D:
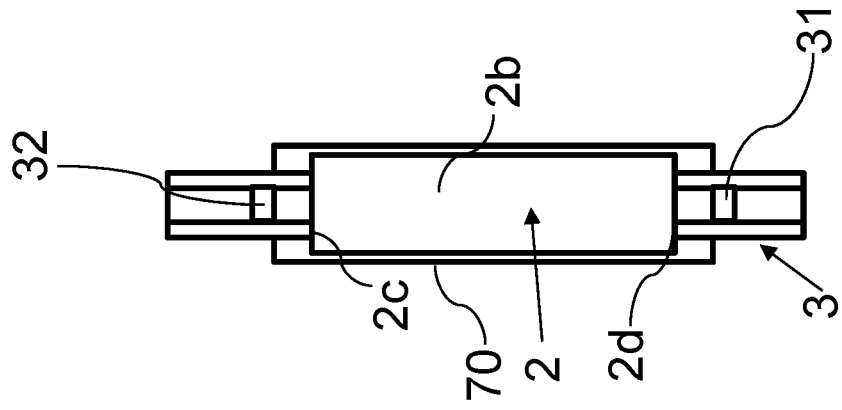

As is shown in FIG. 8(A), it is provided that the respective contact element 40, 41 is moved out of a first position toward the balloon catheter 3 into a second position, so that the respective contact element 40, 41 reaches behind a face 2c of the stent 2 with the protective sheath 70 between them, or is opposite the stent 2 in the axial direction z (see FIG. 8(B)).

Figure 8C:
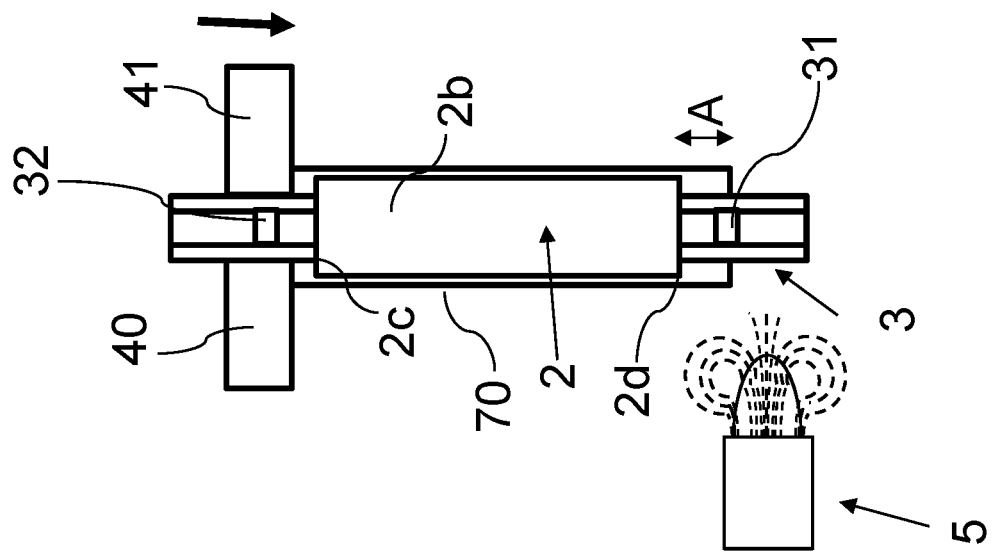

Then, the contact elements 40, 41 are moved in the axial direction z with respect to the balloon 30 of the balloon catheter 3, the contact elements 40, 41 bumping against the stent with the protective sheath 70 between them, and moving the stent into its final position (see FIG. 8(C)). After this, the catheter 3 can be removed from the contact elements 40, 41 (see FIG. 8(D)). Such a movement can also be achieved by a system in which the contact elements 40 and 41 can be designed to grip, e.g., a middle section with the protective sheath 70 between them, analogous to the system shown in FIG. 7.

The distance A between the stent end 2d and the distal X-ray marker 31 as the stent 2 is moved is preferably monitored by a capacitive or inductive sensor 5.

Preferably, this involves first fixing the catheter 3, so that it can only move in the axial direction z, in order to receive a sensor signal that is as stable as possible. After this, the balloon catheter 3 is moved in the axial direction z or the sensor 5 is moved until the X-ray marker 31 (in particular its proximal edge) and the distal stent end 2d are detected. Then, the balloon catheter 3 is fixed in the axial direction z. After this, the contact elements 40, 41 perform the above-described repositioning of the stent 2 in the axial direction z until the distance A between the stent end 2d and the X-ray marker 31 reaches a desired value (the distance between the two X-ray markers 31, 32 and the length of the stent 2 in the axial direction z are known).

The invention advantageously allows machine repositioning of a pre-crimped drug-coated stent 2 and prevents its contamination in the process.

The inductive or capacitive sensor 5 makes it possible to avoid the susceptibilities to error of optical detection having to do with the protective sheath, especially in the case of a non-transparent protective sheath. For instance, contamination on the balloon 30 can lead to optical measurement errors. In addition, the balloon folds of the balloon 30 lie adjacent to the X-ray markers 31, 32, and they can lead to reflections, which can make optical detection of the markers 31, 32 difficult. Thus, non-optical detection by an inductive or capacitive sensor 5 has advantages even for non-encapsulated stents 2.

The invention claimed is:

1. A process for repositioning a drug-coated stent that is pre-crimped on a balloon of a balloon catheter extending in an axial direction so that an inner surface of the stent lies against an outer surface of the balloon, the process comprising:
gripping the stent with at least one contact element and a protection device between the stent and the at least one contact element to prevent contact between the stent and the at least one contact element;
moving the stent with the at least one contact element in the axial direction with respect to the balloon of the balloon catheter to reposition the stent with respect to the balloon.

2. A process according to claim 1, wherein the at least one contact element is moved out of a first position toward the balloon catheter into a second position to reach behind a face of the stent with the protection device positioned between the stent and the at least one contact element.

3. A process according to claim 2, wherein the at least one contact element comprises a tapering end section configured to reach behind the stent.

4. A process according to claim 1, wherein the at least one contact element is moved out of a first position toward the balloon catheter into a second position that presses the protection device against the stent.

5. A process according to claim 4, wherein the at least one contact element located in the second position is moved in the axial direction along the balloon catheter carrying the stent while the balloon catheter is fixed with respect to the axial direction.

6. A process according to claim 5, wherein the at least one contact element moves the stent in the axial direction until the distance in the axial direction from one end of the stent to an X-ray marker arranged on the balloon catheter corresponds to a predetermined distance.

7. A process according to claim 6, wherein the predetermined distance is monitored with one or more of a camera, a capacitive sensor, and an inductive sensor.

8. A process according to claim 1, wherein the protection device comprises at least one film.

9. A process according to claim 8, comprising moving the at least one film after it makes contact with the stent and the stent is moved in the axial direction so that a next stent to be repositioned makes contact with a new section of the at least one film.

10. A process according to claim 9, wherein the least one film is moved in the axial direction.

11. A process according to claim 9, wherein the at least one film is moved in a direction orthogonal to the axial direction.

12. A process according to claim 9, wherein the at least one film is moved by unwinding the at least one film from a feed roller and winding it up onto a take-up roller.

13. A process according to claim 1, wherein the at least one contact element comprises multiple contact elements and the protection device comprises multiple films, wherein each of the multiple contact elements grips the stent with a respective one of the multiple films between it and the stent, and each of the multiple contact elements is moved into a first position toward the balloon catheter and into a second position to behind a face of the stent with its respective film between it and the stent.

14. A process according to claim 13, wherein the at least one contact element comprises multiple contact elements and the protection device comprises multiple films, wherein each of the multiple contact elements grips the stent with a respective one of the multiple films between it and the stent by pressing its respective film against the stent.

15. A process according to claim 1, wherein the protection device is formed by a protective sheath arranged on the stent and surrounding the stent, the at least one contact element gripping the stent with the protective sheath between the at least one contact element and the stent to prevent contact between the stent.

16. A process according to claim 15, wherein the at least one contact element comprises multiple contact elements, wherein each of the multiple contact elements grips the stent with the protective sheath between it and the stent, and each of the multiple contact elements is moved into a first position toward the balloon catheter and into a second position behind a face of the stent with the protective sheath between it and the stent and carries the protective sheath and the stent along with it in the axial direction.

17. A process according to claim 15, wherein the at least one contact element comprises multiple contact elements, wherein each of the multiple contact elements grips the stent with the protective sheath between it and the stent, and each of the multiple contact elements is moved into a first position toward the balloon catheter and into a second position pressing the protective sheath against the stent.

18. A process according to claim 1, wherein the at least one contact element moves the stent in the axial direction until the distance in the axial direction from one end of the stent to an X-ray marker arranged on the balloon catheter corresponds to a predefined distance as determined by a capacitive or inductive sensor.

19. A process according to claim 18, wherein before the stent is moved in the axial direction, the balloon catheter is moved in the axial direction with respect to the sensor until the sensor detects the X-ray marker and the one end of the stent.

\* \* \* \* \*